United States Patent
Lombardi et al.

(10) Patent No.: US 7,901,904 B2
(45) Date of Patent: Mar. 8, 2011

(54) METHOD AND INTERMEDIATES FOR PREPARING 2-ALKOXY AND 2-ARYLOXY ESTROGEN COMPOUNDS

(75) Inventors: Paolo Lombardi, Cesate (IT); Franco Buzzetti, Monza (IT)

(73) Assignee: Naxospharma S.R.L., Cesate (IT)

( * ) Notice: Subject to any disclaimer, the term of this patent is extended or adjusted under 35 U.S.C. 154(b) by 141 days.

(21) Appl. No.: 12/285,901

(22) Filed: Oct. 16, 2008

(65) Prior Publication Data
US 2010/0099141 A1    Apr. 22, 2010

(51) Int. Cl.
*C12P 33/00*    (2006.01)
*C07J 1/00*    (2006.01)
(52) U.S. Cl. ............................ 435/52; 552/502; 552/632
(58) Field of Classification Search .................... 435/52; 552/502, 632
See application file for complete search history.

(56) References Cited

FOREIGN PATENT DOCUMENTS
WO    WO 98/40398 A1    9/1998

OTHER PUBLICATIONS

Metcalf et al. Tetrahedron Lett. (1980) 21: 15-18.*
Rao, P. Narasimha et al: "Synthesis of 2-hydroxy-17.beta.-estradiol" 1960, Tetrahedron, 10, 144-7.
Database HCAPLUS [Online] Chemical Abstracts Service, Columbus, Ohio, US; 1960, Axelrod, L. R. et al: "Synthesis of 2-hydroxy-17.beta.-estradiol", Chem & Pharm. Bull. (1972) 20(7): 1417-23.
Database HCAPLUS [Online] Chemical Abstracts Service, Columbus, Ohio, US; 1972, Yoshizawa, Itsuo et al: "Reactivity of two hydroxyl groups of catechol estrogen", Chem & Industry (1959) 1454-5.

* cited by examiner

*Primary Examiner* — Sandra Saucier
*Assistant Examiner* — Susan Hanley
(74) *Attorney, Agent, or Firm* — Modiano & Associati; Daniel O'Byrne; Albert Josif

(57) ABSTRACT

The present invention relates to a method for preparing 2-alkoxy and 2-aryloxyestrogen compounds, and the intermediate compounds prepared during the use of this method, which intermediate compounds are useful intermediates in the preparation of certain physiologically active compounds.

9 Claims, No Drawings

METHOD AND INTERMEDIATES FOR PREPARING 2-ALKOXY AND 2-ARYLOXY ESTROGEN COMPOUNDS

The subject of the present invention is a method for preparing 2-alkoxy and 2-aryloxyestrogen compounds, and the intermediate compounds prepared during the use of this method, which intermediate compounds are useful intermediates in the preparation of certain physiologically active compounds.

BACKGROUND OF THE INVENTION 2-alkoxyestrogen derivatives are steroid compounds which have or might have therapeutic value. In this respect, 2-methoxyestradiol, a physiological urinary metabolite of endogenous estradiol, has been reported to be an anticancer agent of high clinical relevance for many tumour types.

In U.S. Pat. No. 5,504,074, continuation U.S. Pat. No. 5,661,143 and divisional U.S. Pat. No. 5,892,069 there are claimed methods of treating mammalian diseases characterized by undesirable angiogenesis and abnormal mitosis, respectively, by administering 2-methoxyestradiol.

In U.S. Pat. No. 5,643,900 there is claimed a method of suppressing the growth of solid tumours sustained by angiogenesis in mammals comprising administering 2-methoxyestradiol.

In U.S. Pat. No. 5,958,892 there is claimed a method of treating a patient having a tumour comprising the step of administering a p53 gene in combination with 2-methoxyestradiol.

In WO02/42319 there are claimed compositions and methods for treating mammalian diseases characterized by undesirable angiogenesis by administering 2-methoxyestradiol.

2-Methoxyestradiol is reported to have multiple mechanisms of action, to be orally available, non-toxic, rapidly excreted, non-estrogenic. For a short but comprehensive review, see for example Pharmacotherapy, 23, 165, (2003).

In *J. Med. Chem.* 40, 2323, (1997), 2-ethoxy and 2-(2,2,2-trifluoroethoxy) estradiol analogues with enhanced biological effects are disclosed.

In *J. Med. Chem.* 47, 5126, (2004), certain 17 alkyl derivatives of 2-methoxyestradiol with enhanced metabolic stability are reported.

Processes for the preparation of 2-methoxyestradiol are known, and all refer to two general methodologies for the preparation of 2-alkoxyestrogens from estradiol or estrone as starting materials.

One methodology entails generally the halogenation at C-2 of a suitably protected estradiol or estrone followed by a nuclophilic displacement of the halogen atom by the alkoxy moiety. A variety of conditions have been employed. See, for example, U.S. Pat. No. 6,051,726; U.S. Pat. No. 6,054,598; *Hunan Daxue Xuebao, Ziran Kexueban* 24, 40, (1997) (C.A. 128:180572); *Sichuan Daxue Xuebao, Ziran Kexueban* 27, 106, (1990) (C.A. 114:6922); *Youji Huaxue* 9, 266, 1989 (C.A. 111:195225); *Steroids* 471, 63-6 (1986); *Sichuan Daxue Xuebao, Ziran Kexueban* 114, (1986) (C.A. 107:176307); *J. Chem. Res., Synop.* 348, (1985); *J. Chem. Soc., Chem. Commun.* 533, (1983); *Synthesis* 168, (1977). Besides the need of protection/deprotection steps, the aromatic halogenation reaction provides also varying amounts of 4- and 2,4-halogenated intermediates in addition to the desired 2-halogen regioisomer, which consequently should be carefully separated from the unwanted regioisomers before proceeding in the synthesis.

The second methodology entails generally the aromatic acylation at C-2 of a suitably protected estradiol or estrone obtained by either a Friedel Craft-type direct acylation or the above mentioned haloderivative. In both cases, mixture of regioisomers may be obtained. A Baeyer-Villiger oxidation follows to provide a 2-acyloxy derivative, which is hydrolized and the resulting phenolic moiety is etherified with a suitable alkylating agent. A variety of conditions have been employed. See, for example, U.S. Pat. No. 6,051,726; U.S. Pat. No. 6,054,598; *Synth. Commun.* 28, 4431, 1998; *Bioorg Med. Chem. Lett.* 4, 1725, (1994); *J. Am. Chem. Soc.* 80, 1213, (1958). The desired product is obtained after a deprotection step.

Neither 2-aryloxyestrogen compounds nor their methods of preparation have been previously disclosed.

Since estradiol and 19-nortestosterone (nandrolone) are commercially available bulk materials which are similarly quoted on the global market, we addressed the practical issue of using 19-nortestosterone as an alternative starting material in lieu of estradiol/estrone, and have now found a process route to 2-alkoxy and 2-aryloxy derivatives of estradiol and estrone starting from 19-norsteroid derivatives. The instant route, entailing advantageously a straightforward aliphatic chemistry with no use of any protecting group, implies the aromatization of the ring A of the 2-alkoxy (aryloxy)-19-norsteroid derivative as the ultimate step. In addition, certain of the process intermediates may have therapeutic applications or are physiological precursors to therapeutic agents.

SUMMARY OF THE INVENTION

The subject of the invention is a method for preparing compounds of general formula (I):

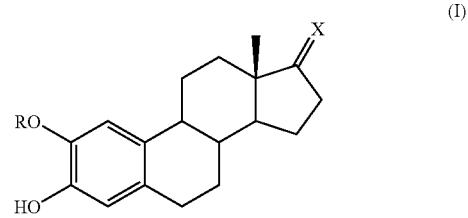

wherein X is a member of the group consisting of O and

wherein $R_a$ is H, lower alkyl, alkenyl and alkynyl radical; and R represents:
a linear, branched or cyclic alkyl radical containing from 1 to 8 carbon atoms, which may be further optionally substituted with 1-3 substituents chosen among the group consisting of
  (a) halogen,
  (b) $OR_b$, wherein $R_b$ represents H, lower alkyl, and aryl,
  (c) (C1-C6) cycloalkyl, optionally substituted with 1-3 substituents such as halogen, lower alkyl, aryl, or $OR_b$,
  (d) (C6-C10) aryl, optionally substituted with 1-3 substituents such as halogen, lower alkyl, aryl, or $OR_b$,
  (e) (C6-C10) heteroaryl, optionally substituted with 1-3 substituents such as halogen, lower alkyl, aryl, or $OR_b$, an aryl radical containing from 6 to 10 carbon atoms, which may be further optionally substituted with 1-3 substituents chosen among the group consisting of
  (a) halogen,
  (b) $OR_b$, wherein $R_b$ represents H, lower alkyl, and aryl,
  (c) (C1-C6) linear, branched or cyclic alkyl, optionally substituted with 1-3 substituents such as halogen, lower alkyl, aryl, or $OR_b$, comprising the following steps:
  (1) subjecting a compound of formula (II)

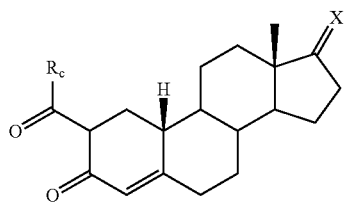

(II)

wherein X being as defined above, with the proviso that X does not represent O, and
$R_c$ represents:
  H;
  trifluoromethyl;
  phenyl, optionally substituted with fluoro, chloro, nitro, methoxy; or (lower)alkoxycarbonyl;
to a diazo transfer reaction with a sulfonyl azide derivative so as to obtain a compound of formula (III)

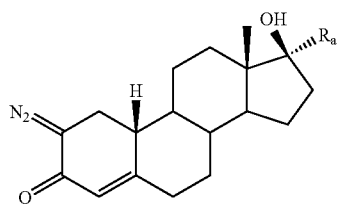

(III)

wherein X being as defined above, with the proviso that X does not represent O;
  (2) treating the compound of formula (III) with a transition metal compound, salt or complex, such as a compound, salt or complex of, for example, Rh, Cu or Ru in presence of a hydroxy compound of formula ROH, R being as defined above, so as to obtain a compound of formula (IV)

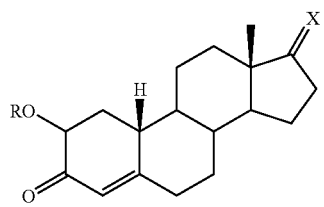

(IV)

wherein R being as defined above, and X represents the group;

;and, if desired, the compound of formula (IV) so obtained in step (2) when $R_a$ represents hydrogen may be optionally oxidized into a compound of formula (IV) wherein X represents O;
  (3) the compound of formula (IV), wherein R and X being as defined by all the meanings above is treated with an aromatization agent so as to obtain a compound of formula (I), R and X being as defined above;
and, if desired, as an optional part of the step (3), a compound of formula (I), R being as defined above and X represents the group

wherein $R_a$ represents hydrogen, may be oxidized into a compound of formula (I) wherein X represents O, and this compound of formula (I) so obtained wherein X represents O, may be transformed into a compound of formula (I), X being as defined by the group

$R_a$ being as defined above.

DESCRIPTION OF THE PREFERRED EMBODIMENTS

As a non-limitative example of lower alkyl, alkenyl or alkynyl radicals which $R_a$ may represent, there may be mentioned methyl, ethyl, ethenyl and ethynyl radicals.

As a non-limitative example of a linear, branched or cyclic alkyl radical containing from 1 to 8 carbon atoms which R may represent, there may be mentioned methyl, ethyl, propyl, butyl, pentyl, hexyl and octyl radicals, the branched isomers of these radicals isopropyl, isobutyl, isopentyl, neopentyl, isohexyl, 3-methylpentyl, sec-butyl, tert-butyl and tert-pentyl, and the cyclic isomers of the radicals cyclopropyl, cyclobutyl, cyclopentyl and cyclohexyl.

As a non-limitative example of a linear, branched or cyclic alkyl radical containing from 1 to 8 carbon atoms which may be further optionally substituted with 1-3 substituents chosen among the groups (a)-(e) as previously indicated which R may represent, there may be mentioned:
  (a) 2,2,2-trifluoroethyl;
  (b) 2-methoxyethyl, 2-phenoxyethyl;
  (c) cyclopropylmethyl, cyclopropylethyl, cyclohexylmethyl, (4-methylcyclohexyl)methyl, (4-chlorocyclohexyl)methyl, (4-fluorocyclohexyl)methyl, (4-methylcyclohexyl)methyl, (4-phenylcyclohexyl)methyl, (4-methoxycyclohexyl)methyl, (4-phenoxycyclohexyl)methyl;
  (d) benzyl, o-, m-, and p-chlorobenzyl, o-, m-, and p-fluorobenzyl, 4-methylbenzyl, 4-(o-, m-, and p-methoxyphenyl)benzyl, -o-, m-, and p-methoxybenzyl, 3,4-dimethoxybenzyl, 3,4,5 trimethoxybenzyl, 1-naphthylmethyl, 2-naphthylmethyl;

(e) pyridinemethyl, furanmethyl, N-(loweralkyl)pyrrolemethyl, oxazolemethyl, benzofuranmethyl.

As a non-limitative example of an aryl radical containing from 6 to 10 carbon atoms, which R may represent, there may be mentioned phenyl, 1-naphthyl, 2-naphthyl radicals.

As a non-limitative example of an aryl radical containing from 6 to 10 carbon atoms, which may be further optionally substituted with 1-3 substituents chosen among the groups (a)-(c) as previously indicated which R may represent, there may be mentioned:
- (a) (o-, m-, and p-chloro)phenyl, (o-, m-, and p-fluoro) phenyl;
- (b) (o-, m-, and p-methoxy)phenyl, 3,4-dimethoxyphenyl, 3,4,5-trimethoxyphenyl, (o-, m-, and p-phenoxy)phenyl;
- (c) o-, m-, and p-tolyl, (o-, m-, and p-ethyl)phenyl, (o-, m-, and p-trifluoromethyl)phenyl, 4-(2-methoxyethyl)phenyl.

The subject of the invention is a method for preparing, as defined above, compounds of general formula (I), more particularly in which R represents $CH_3$, $CH_3CH_2$ or $CF_3CH_2$, X being as defined by the group,

,most particularly for preparing the antitumour agent 2-methoxyestradiol.

According to the stepwise method of the present invention, in the step (1) a compound of formula (II)

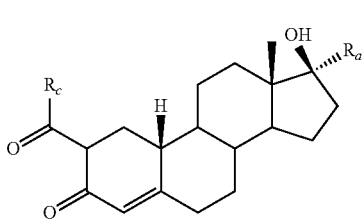

$R_c$ and $R_a$ being as defined above, is subjected to a diazo transfer reaction with a sulfonyl azide derivative so as to obtain a compound of formula (III)

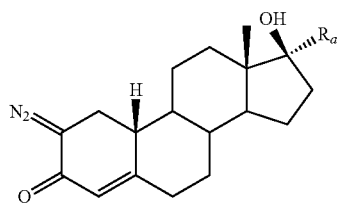

$R_a$ being as defined above.

The diazo transfer reaction is a standard reaction which is carried out according to methods known to persons skilled in the art. As for the steroid field, the diazo transfer reaction has been disclosed for instance in U.S. Pat. No. 4,317,817 for the obtaining of a 4-diazosteroid. 21-diazosteroid derivatives are disclosed in U.S. Pat. No. 2,832,772 and a 16-diazoestrone is disclosed in J. Org. Chem. 38, 3525 (1973). 2- and 4-diazosteroid analogues have been reported also in J. Org. Chem. 32, 2644 (1967), but obtained with a different procedure.

As for the sulfonyl azide reagent, any sulfonyl azide derivative known in the art and/or commercially available can be used. As illustrative, non-limitative examples the following benzenesulfonyl azide, methanesulfonyl azide, 4-toluenesulfonyl azide, 4-dodecylbenzenesulfonyl azide, 4-acetamidobenzenesulfonyl azide, 2,4,6-triisopropylbenzenesulfonyl azide, trifluoromethanesulfonyl azide, 4-carboxybenzenesulfonyl azide, 4-nitrobenzenesulfonyl azide and imidazole-1-sulfonyl azide may be cited.

A compound of formula (IIa) is easily prepared starting from a suitable steroid by a Claisen-type acylation reaction. Preferred starting steroids are 19-nortestosterone (nandrolone), 17alpha-ethyl-19-nortestosterone (norethandrolone), 17alpha-methyl-19-nortestosterone (normethandrone), 17alpha-ethynyl-19-nortestosterone (norethyndrone). The Claisen-type acylation reaction is a standard reaction which has been carried out in the steroid field according to methods known to persons skilled in the art, for instance as described in J. Med. Chem. 37, 4227 (1994), and in J. Am. Chem. Soc. 82, 2840 (1960).

Any suitable acylating agent may be used. As acylating agents, preferred are the lower alkyl esters of formic, benzoic, p-nitrobenzoic, oxalic acids, most preferred are ethyl formate and diethyl oxalate. Claisen-type acylations are promoted by bases, such as the lower alkoxides of alkali metals, for instance sodium methoxide or sodium ethoxide, and are generally carried out in apolar solvents, from where the product separates as a precipitate in the form of the enolate salt. Since the above diazo transfer reaction has to be carried out in basic media, an advantageous aspect of the subject step of the present process provides the isolation and purification of the compound of formula (II) from the Claisen-type acylation in the form of the precipitated di-salt of formula (IIa), $M^+$ being the cation of an alkali metal, for instance sodium,

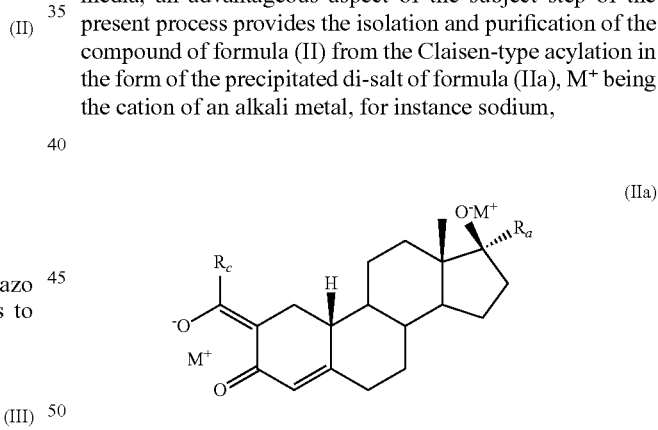

and the direct reaction of the compound salt of formula (IIa) so obtained with the sulfonyl azide. The choice of the solvent is not critical. There can be used lower alkanols, linear and cyclic alkyl ethers, chlorinated solvents, water, and the mixtures thereof.

According to the stepwise method of the present invention, in the step (2) the diazosteroid of formula (III), $R_a$ being as defined above, is exposed to the catalysis of a transition metal compound, salt or complex, such as a compound, salt or complex of Rh, Cu or Ru, in presence of a hydroxy compound of formula ROH, R being as defined above, in a suitable inert solvent. This results in the decomposition of the diazo functional group which leaves the reaction media as gaseous nitrogen, with insertion of the RO moiety, so as to obtain a compound of formula (IVa)

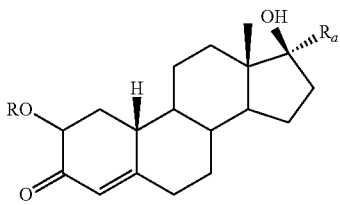

(IVa)

Although this type of intermolecular C—O bond formation is documented in the scientific literature (reviewed for example in *Tetrahedron,* 51, 10811, (1995)), and both in *Helv. Chim. Acta,* 33, 417, (1950), for example, and in the above cited U.S. Pat. No. 2,832,772 the insertion of an oxy group following the decomposition of a primary diazo group in the side chain of a steroid is disclosed, there is no knowledge or teaching about the intermolecular RO— insertion onto a secondary and cyclic carbon following decomposition of the corresponding diazo group. In the documents referring to the disclosure of 2- and 4-diazosteroids, previously cited, there is no mention of further chemical transformation of the diazo groups.

As for the transition metal compound, salt or complex such as of, for example, Rh, Cu or Ru, the following non-limitative derivatives may be cited: dirhodium tetracarboxylates (e.g. the tetraacetate, tetraoctanoate, tetraperfluoropropionate, for a review see *Tetrahedron,* 47, 1765, (1991)); certain dirhodium tetraprolinates (*Tet. Lett.* 37, 4129 & 4133, (1996)); dirhodium tetrakis(acetamide); copper bis(acetylacetonate) (but also other compounds of copper, nickel and lead, as reported in the above cited *Tetrahedron,* 51, 10811, (1995)); ruthenium dichloride tris(triphenylphosphine) (*Tet. Lett.* 37, 8815, (1996)). Such derivatives are either commercially available or easily prepared, and the reaction is carried out in a suitable inert solvent at a temperature which generally may range from −78° C. to 100° C. for from few minutes to 3 days. If desired, an organic amine such as, for example, triethyl amine, diisopropylethyl amine, pyridine, quinoline, and the like may be added to the reaction mixture as an adjuvant.

As a person skilled in the art will appreciate, the introduction of the RO— moiety at C-2 of the steroid will generate a new steric centre and two possible compounds (epimers) of formula (IVa) may be obtained, namely with 2R and 2S configurations or, if preferred, 2alfa and 2beta, with reference to the rule adopted with naturally-occurring steroids. Indeed, in some instances, the two possible epimers are obtained with varying 2R/2S ratios. After having carried out extensive research, we have found that the 2R/2S ratio is dependent on certain empyrical factors such as the nature of the R group, the solvent used, the temperature at which the reaction is performed, the type of transition metal salt or complex used for the decomposition of the diazo group, the relative amount of ROH in the reaction mixture, and the presence, if any, and the nature of the adjuvant amine added.

Optionally, and if desired, after the completion of the above described step (2) of the stepwise method of the present invention, a compound of formula (IVa), wherein $R_a$ represents hydrogen, may be oxidized into a compound of formula (IV), wherein X represents oxygen. This oxidation reaction is a quite standard reaction in the steroid field, which is carried out according to methods known in the art for the oxidation of the 17-hydroxy group to the 17-oxo group, as reported, for example, in U.S. Pat. No. 4,876,045.

According to the stepwise method of the present invention, in the step (3) a compound of formula (IV), wherein R and X being as defined by all the meanings above, is treated with an aromatization agent so as to obtain a compound of formula (I), R and X being as defined above.

The aromatization reaction may be carried out by either chemical or biological agents, as known to a person skilled in the art.

In a first aspect of the step (3) of the stepwise method of the present invention, we have found that this aromatization may be carried out as a dehydrogenation reaction catalyzed by Pd—, Pt—, Rh—, Ru—, or Ni-based conventional hydrogenation catalysts in the presence of suitable hydrogen acceptors such as cyclohexene, cyclooctene, dialkyl maleates or any other commercially available high boiling olefin, or nitrohydrocarbons, such as nitrobenzene, in a suitable inert solvent at a temperature from 80° C. to 180° C., generally at the refluxing point of the appropriate solvent/hydrogen acceptor mixture, for a time from 6 hours to 4 days. This catalyzed dehydrogenation reaction has been widely and efficiently applied in the steroid field, as disclosed, for example, in U.S. Pat. Nos. 3,44,9327, 3,458,502, 3,484,435 and 3,494,918.

In certain cases of this first aspect of the step (3) of the invention, the catalyzed dehydrogenation reaction provides superior yields when performed in presence of a base, such as aqueous sodium or potassium hydroxides, carbonates and the like. Surprisingly, we found that certain compounds of formula (IV), when exposed to the action of the above mentioned bases, are transformed into compounds possessing the "unnatural" stereochemistry at C-10 represented by the formula (IVb)

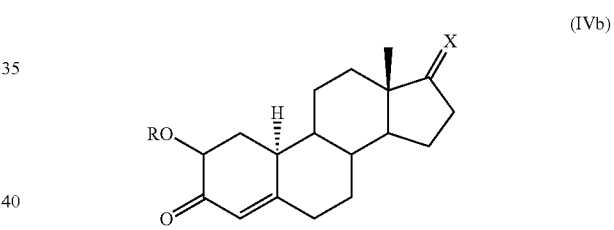

(IVb)

wherein R and X being as defined by all the meanings above, which undergo the above mentioned catalyzed dehydrogenation reaction rapidly and in high yield.

In a second aspect of the step (3) of the stepwise method of the present invention, we have also found that this aromatization may be carried out as a quinone-mediated dehydrogenation reaction, for example a dehydrogenation by 2,3-dichloro-5,6-dicyanobenzoquinone (DDQ) in an suitable inert solvent under neutral or weakly acidic conditions, at a temperature from 60° C. to 120° C., generally at the refluxing point of the solvent, for a time from 1 to 24 hours. This DDQ-mediated dehydrogenation reaction has been widely and efficiently applied in the steroid field (see, for example, *Chem. Rev.* 1967, 153).

In a third aspect of the step (3) of the stepwise method of the present invention, we have also found that this aromatization may be carried out by the oxidative action of selenium dioxide ($SeO_2$), a reagent widely used for the introduction of the 1,2-double bond in the A-ring of a steroid (U.S. Pat. Nos. 3,203,965 and 3,211,725).

In a forth aspect of the step (3) of the stepwise method of the present invention, we have also found that this aromatization may be carried out by the action of $CuBr_2$—LiBr, as disclosed in *Tet. Lett.* 10, 821 (1977) for the specific case of a 19-norsteroid.

In a fifth aspect of the step (3) of the stepwise method of the present invention, we have also found that this aromatization may be carried out by subjecting a compound of formula (IV) to the action of enzymes from 1-dehydrogenating microorganisms. Methods, enzymes and microorganisms useful to achieve this steroidal A-ring 1-dehydrogenation reaction leading to a 1,2-dehydrosteroid which, as a person skilled in the art will appreciate, in the instant case continues to undergo aromatization so that to obtain a compound of formula (I) are described, for example, in U.S. Pat. Nos. 2,928,850, 3,047, 469, 3,517,036, and 4,684,610; in *J. Am. Chem. Soc.* 75, 5764, (1953), *J. Biol. Chem.* 234, 2009 & 2014, (1959), *Tetrahedron* 18, 581 & 591, (1962), *Biochem.* 4, 2113, (1965), *J. Org. Chem.* 31, 2512, (1966), and *Biochim. Biophys. Acta,* 1038, 60, (1990). As non-limitative examples of 1-dehydrogenating microorganisms the following *Bacterium cyclooxidans, Corynebacterium simplex, Corynebacterium hoagii, Cylindrocarpon radicicola, Mycobacterium rhodocrous, Nocardia restrictus, Nocardia rhodocrous, Nocardia corallina, Nocardia coeliaca, Nocardia globerula, Nocardia aurantia, Pseudomonas testosteroni, Septomyxa affinis* may be cited.

Optionally, and if desired, after the completion of the above described step (3) of the stepwise method of the present invention, a compound of formula (I), wherein X represents

wherein $R_a$ represents hydrogen, may be oxidized into a compound of formula (I), wherein X represents oxygen, and this compound of formula (I) so obtained wherein X represents O, may be transformed into a compound of formula (I), X being as defined by the group,

,$R_a$ being as defined above. Such transformations require quite standard reactions in the steroid field, which are carried out according to methods well known in the art.

A relevant aspect of this invention is that we found that certain of the compounds of formula (IV) and formula (IVb) are aromatized by aromatizing enzymes of mammalian source. That 19-nortestosterone derivatives are readily aromatized in vivo and that this aromatization is carried out by certain members of the cytochrome P450 enzyme superfamily (CYP) which are expressed in many tissues (including tumors) is a well known phenomenon. The most relevant mammalian enzyme is the ubiquitous cytochrome P450 aromatase, which has been reported to process both C-19 and 19-nor steroid substrates providing the aromatization of the A-ring (*Biochemistry* 7, 33, (1968); *Nippon Naibunpi Gakkai Zasshi* 62, 18, (1986); *J. Biol. Chem.* 262, 5717, (1987); *J. Endocrinol.* 120, 251, (1989); *J. Steroid Biochem.* 32, 537, (1989); *J. Steroid Biochem.* 32, 729, (1989); *J. Steroid Biochem.* 33, 949, (1989); *J. Steroid Biochem.* 48, 297, (1994); *J. Endocrinol.* 144, 517, (1995)). However, the action of the cytochrome P450 aromatase may be not necessary and the oxidative introduction of double bonds into the A-ring of 19-nor steroids leading to the aromatization of A-ring can be catalyzed by other cytochrome P450 enzymes, for example hepatic cytochrome P450 enzymes (*Endocrinol Jpn* 33, 527, (1986); *Nippon Sanka Fujinka Gakkai Zasshi* 40, 87, (1988); *Climateric,* 10, 344, (2007)).

The following examples are included for purposes of illustration only and are not to be construed as limitations herein.

EXAMPLES

Example 1

General Preparation of 2-acyl-19-nortestosterone Derivatives (II)

Following published procedures, by applying some modifications, the compounds were prepared by combining the 19-nortestosterone derivative with 2.5 molar equiv. of freshly prepared sodium methoxide in toluene under a nitrogen atmosphere. After stirring at room temperature for 30 min, 2.5 molar equiv. of the ester were added and the reaction mixture was allowed to stir for additional 12 hours. The resulting suspension was diluted with a mixture of diethyl ether-toluene, and filtered. The filter cake was washed several times with the above solvent mixture, then with diethyl ether, and dried under reduced pressure to give the enolate salt which was stored to be directly used as such in the next step.

Example 2

2-diazo-19-nortestosterone (III, $R_a$=H)

1.38 g (ca. 3.3 mmol) of crude 2-ethoxalyl-19-nortestosterone sodium enolate (or the molar equivalent of 2-formyl-19-nortestosterone) from Example 1 was dissolved in water (5 ml) and washed with dichloromethane (2×3 ml) in order to extract any unwanted organic material. The aqueous phase was transferred in a reaction vessel and added with 1M KOH solution (3.3 ml) and tetrahydrofuran (15 ml). To the stirred reaction mixture, 4-toluenesulfonyl azide (0.650 g, 3.3 mmol) dissolved in tetrahydrofuran (7 ml) was added dropwise. The reaction mixture was stirred for 24 hours at room temperature, after which time the precipitated 4-toluenesulfonyl acyl imide sodium/potassium salt was filtered off and washed with diethyl ether. The combined filtrate and washings were washed with 0.5 N NaOH aqueous solution, brine, dried over sodium sulfate, filtered and evaporated under reduced pressure to yield an oily residue which was dissolved in dichloromethane and precipitated by adding hexanes to furnish the title product as a light yellow solid (0.590 g).

IR (CHCl$_3$, cm$^{-1}$): 2100, 1650

NMR (200 MHz, d, CDCl$_3$): 5.85(1H, br s), 3.68(1H, t), 2.98(1H, dd), 2.61(1H, dd), 2.55-0.9 (17H, m), 0.82(3H, s).

Example 3

2-methoxy-19-nortestosterone (IVa, R=CH$_3$, $R_a$=H)

To dirhodium tetraacetate (0.0044 g) in dichlomethane (4 ml) were added diisopropylethylamine (0.032 g) and methanol (0.032 g). To the resulting stirred suspension was added under nitrogen at 0-5° C. 2-diazo-19-nortestosterone (0.130 g) of Example 2 dissolved in dichlomethane (4 ml), dropwise in 15 min. The reaction mixture was allowed to stir for further 2 hour, filtered on a pad of celite which was extensively washed with dichlorometane. The combined dichlomethane filtrate and washings were washed with water, dried over calcium chloride, filtered and evaporated under reduced pressure to give a solid residue which, as judged by TLC (40:1 dichloromethane/methanol), was composed of the two C-2 epimers of the title compound at Rf=0.30 and Rf=0.23, respectively, in a 9:1 approx. ratio.

The epimeric mixture was separated by column chromatography on silica gel (1:1 hexane/ethyl acetate):

fast eluting epimer (Rf=0.30, 40:1 dichloromethane/methanol):

NMR (200 MHz, d, CDCl$_3$): 5.78 (1H, t, J=1.5 Hz), 3.75 (1H, dd), 3.65(1H, t), 3.56(3H, s), 2.5-0.9(17H, m), 0.80(3H, s);

slow eluting epimer (Rf=0.23, 40:1 dichloromethane/methanol):

NMR (200 MHz, d, CDCl$_3$): 5.88 (1H, br s), 4.10(1H, dd), 3.65(1H, t), 3.56(3H, s), 2.5-0.9(17H, m), 0.80(3H, s).

The combined total weight of the two epimers was 0.075 g.

By substituting dirhodium tetraoctanoate for dirhodium tetraacetate and operating in the same way as above, the two epimers were obtained in a (Rf=0.30)/(Rf=0.23)=approx 5:5.

Example 4

2-Methoxyestradiol by Catalytic Dehydrogenation

To 0.500 g of a mixture of the two C-2 epimers obtained as in Example 3 dissolved in dioxane (30 ml) were added 10% Pd/C catalyst (0.250 g) and cyclohexene (10 ml). Under nitrogen, the resulting reaction mixture was vigorously stirred at reflux. The reaction was monitored by TLC (40:1 dichloromethane/methanol) and after 8 hours the analysis showed the disappearance of the epimer at Rf=0.23 and the formation of a new product migrating at Rf=0.41, which resulted positive to the ferric chloride/potassium ferricyanide test. Since at this stage the reaction seemed to be sluggish or not to proceed any further, potassium hydroxyde (0.6 ml of a 1N aqueous solution) was added and the reaction mixture was stirred and refluxed for additional 12 hours, after which time the epimer at Rf=0.30 has disappeared and the product at Rf=0.41 increased. The cooled reaction mixture was neutralized by adding hydrochloric acid (0.6 ml of a 1N aqueous solution), the catalyst was filtered off and washed with dioxane. The filtrate was evaporated to dryness under reduced pressure and the resulting residue chromatographed on silica gel column (8:2 hexane/ethyl acetate) to give 2-methoxyestradiol (0.300 g).

NMR (200 MHz, d, CDCl$_3$): 6.79 (1H, s), 6.64 (1H, s), 5.40 (1H, s), 3.85(3H, s), 3.70 (1H, t), 2.75(2H, m), 2.25-1.1(13H, m), 0.81(3H, s).

Example 5

2-methoxy-10-epi-19-nortestosterone (IVb, R=CH$_3$,

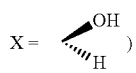

This example was aimed at understanding the finding of Example 4. 2-Methoxy-19-nortestosterone (epimer at Rf=0.30, 0.050 g) was refluxed in dioxane (5 ml) in presence of potassium hydroxyde (0.06 ml of a 1N aqueous solution). After 3 hours, TLC analysis (95:5 dichloromethane/ethanol) showed that the starting material equilibrated (approx. 1:1) to a product migrating at a slightly higher Rf. The reaction mixture was then cooled and evaporated to dryness under reduced pressure, and the residue chromatographed (8:2 hexane/ethyl acetate) to yield, as a first eluting, a product to which was tentatively assigned the structure of the C-10 epimer of the starting material based on its NMR data.

NMR (200 MHz, d, CDCl$_3$): 5.78 (1H, br s), 3.65(1H, t), 3.50(1H, dd), 3.38(3H, s), 2.5-0.9 (17H, m), 0.78(3H, s).

Example 6

2-Methoxyestradiol by Dichlorodicyanobenzoquinone Oxidation 0.050 g of 2-methoxy-19-nortestosterone and 0.057 g of dichlorodicyanobenzoquinone were refluxed in 10 ml of anhydrous dioxane for about 15 hours. To remove the DDQ the suspension was filtered through alumina. After evaporation of the solvent the residue was dissolved in ethyl acetate, the organic layer washed with water, dried over sodium sulfate and the solvent removed under reduced pressure. The crude product was chromatographed as reported in Example 4 to yield 0.020 g of 2-methoxyestradiol.

Example 7

2-Methoxyestradiol by Selenium Dioxide Oxidation

A mixture of 2-methoxy-19-nortestosterone (0.050 g), selenium dioxide (0.050 g), tert-butanol (20 ml) and 0.1 ml pyridine was heated at reflux under nitrogen for about 30 hours. The cooled solution was filtered and then evaporated to dryness under reduced pressure. The residue was taken up in ethyl acetate (20 ml), treated with charcoal, filtered and washed with water, ammonium sulfide aqueos solution, cold 17% ammonium hydroxide, cold dilute hydrochloric acid, water, dried over sodium sulfate and finally evaporated to dryness under reduced pressure. The crude product was chromatographed as described in Example 4 to yield 0.025 g of 2-methoxyestradiol.

Example 8

2-Methoxyestradiol by Action of CuBr$_2$—LiBr

A mixture of 2-methoxy-19-nortestosterone (0.050 g), CuBr$_2$ (0.135 g), LiBr (0.015 g) and acetonitrile (25 ml) was heated at reflux under nitrogen for 30 min, after which time the heating was stopped and cold water was added to the reaction mixture. The cold reaction mixture was filtered, the organic layer separated and the aqueous layer extracted twice with ethyl acetate. The combined organics were washed with water and dried over sodium sulfate and finally evaporated to dryness under reduced pressure. The crude product was chromatographed as described in Example 4 to yield 0.030 g of 2-methoxyestradiol.

Example 9

2-Methoxyestradiol by Microbiological Transformation

Following the procedure reported in U.S. Pat. No. 3,517,036, 2 mg of 2-methoxy-19-nortestosterone are combined with a cell-free enzyme preparation from *Corynebacterium simplex*. At the end of the incubation period, the mixture is extracted with methyl isobutyl ketone. TLC analysis of the combined extracts (40:1 dichloromethane/methanol) showed the presence of 2-methoxyestradiol, confirmed against an authentic reference standard.

Example 10

2-Methoxyestradiol by Placental Preparation (aromatase)

Placental preparations equivalent to those obtainable from 30.7 g of wet tissue, prepared and tested for aromatase activity as described in *J. Biol. Chem.*, 234, 268 (1959) and in *J. Biol. Chem.*, 249, 5364 (1974), respectively, were reconstituted in aromatase phosphate buffer (pH 7.5, 10 mM potassium phosphate buffer, 100 mM KCl, 1 mM EDTA and 1 mM dithiothreitol) and combined with 0.5 mg 2-methoxy-19-nortestosterone, dissolved in propylene glycol, and 25 umol NADPH in a final volume of 15 ml. The resulting mixture was incubated in air for 3 hours at 37° C. under stirring, after which time was extracted with $CHCl_3$ (4×10 ml) and the combined extracts were washed with water and evaporated under reduced pressure. The residue, dissolved in hexane (30 ml), was then extracted with 90% aqueous methanol (3×25 ml) and the combined methanolic extracts were evaporated under reduced pressure to leave a residue which was taken up with toluene (70 ml). The toluene was extracted with 1N NaOH (5×15 ml) and the combined basic extracts were adjusted to pH 8.5 and extracted with ethyl ether. TLC analysis of the ethereal solution (40:1 dichloromethane/methanol) showed the presence of 2-methoxyestradiol, confirmed against an authentic reference standard.

Example 11

2-(p-methoxyphenoxy)-19-nortestosterone (IVa, R=p-($CH_3O$)—$C_6H_4$, $R_a$=H)

The title compound was obtained from 2-diazo-19-nortestosterone, p-methoxyphenol and dirhodium tetraacetate following the same procedure as in Example 3.

NMR (200 MHz, d, $CDCl_3$): 6.98 (2H, d), 6.70 (2H d), 5.80 (1H, br s,), 4.45 (1H, dd), 3.70 (3H, s), 3.65 (1H, t), 2.5-0.9 (17H, m), 0.81 (3H, s).

By substituting 3,4-dimethoxyphenol for p-methoxyphenol and following the same procedure, there was obtained:

2-(3,4-Dimethoxyphenoxy)-19-nortestosterone (IVa, R=3,4-($CH_3O$)$_2$—$C_6H_3$, $R_a$=H)

NMR (200 MHz, d, $CDCl_3$): 6.51 (1H, d), 6.22 (1H s), 6.15 (1H, dd), 5.80 (1H, br s,), 4.45 (1H, dd), 3.70 (6H, s), 3.65 (1H, t), 2.5-0.9 (17H, m), 0.81 (3H, s).

Example 12

2-(p-methoxyphenoxy)estradiol (I, R=p-($CH_3O$) $C_6H_4$,

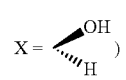
)

The title compound was obtained from 2-(p-methoxyphenoxy)-19-nortestosterone of Example 11 by catalytic dehydrogenation as described in Example 4.

NMR (200 MHz, d, $CDCl_3$): 7.35 (2H, d), 6.80 (2H, d), 6.79 (1H, s) 6.64 (1H, s), 5.40 (1H, s), 3.75(3H, s), 3.70 (1H, t), 2.75(2H, m), 2.25-1.1(13H, m), 0.81(3H, s).

By substituting 2-(3,4-Dimethoxyphenoxy)-19-nortestosterone (IVa, R=3,4-($CH_3O$)$_2$—$C_6H_3$, $R_a$=H) for 2-(p-methoxyphenoxy)-19-nortestosterone (IVa, R=p-($CH_3O$)—$C_6H_4$, $R_a$=H) and following the same procedure, there was obtained:

2-(3,4-Dimethoxyphenoxy)estradiol (I, R=(3-$CH_3O$)(4-$CH_3O$)$C_6H_3$,

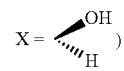
)

NMR (200 MHz, d, $CDCl_3$): 6.79 (1H, s), 6.64 (1H, s), 6.51 (1H, d), 6.22 (1H s), 6.15 (1H, dd), 5.40 (1H, s), 3.75(6H, s), 3.70 (1H, t), 2.75(2H, m), 2.25-1.1(13H, m), 0.81(3H, s).

What is claimed is:
1. A method for preparing compounds of formula (I):

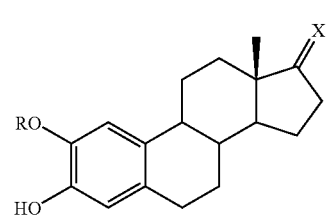

wherein X is a member of the group consisting of O and

wherein $R_a$ is H, lower alkyl, alkenyl or alkynyl;
and R is:
(a) halogen;
(b) $OR_b$, wherein $R_b$ is H, lower alkyl or aryl;
(c) C1-C6 cycloalkyl, optionally substituted with 1-3 substituents selected from the group consisting of halogen, lower alkyl, aryl, and $OR_b$ wherein Rb is H, lower alkyl, and aryl;
(d) C6-C10 heteroaryl, optionally substituted with 1-3 substituents selected from the group consisting of halogen, lower alkyl, aryl, and $OR_b$ wherein Rb is H, lower alkyl, or aryl; or
(e) C6-C10 aryl optionally substituted with 1-3 substituents selected from the group consisting of
(a) halogen;
(b) $OR_b$, wherein $R_b$ is H, lower alkyl, or aryl;
(c) C1-C6 linear, branched or cyclic alkyl, optionally substituted with 1-3 substituents selected from the group consisting of halogen, lower alkyl, aryl, and $OR_b$ wherein Rb is H, lower alkyl, or aryl;
(d) aryl; and
(e) lower alkyl;
comprising the following steps:
(1) subjecting a compound of formula (II)

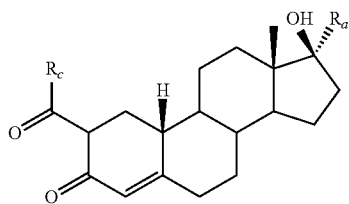

(II)

wherein $R_a$ is H, lower alkyl, alkenyl and alkynyl, and $R_c$ is:
H;
trifluoromethyl;
phenyl, optionally substituted with fluoro, chloro, nitro, methoxy; or
lower alkoxycarbonyl;
to a diazo transfer reaction with a sulfonyl azide derivative to obtain a compound of formula (III)

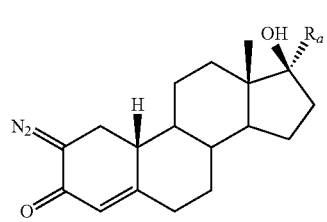

(III)

wherein $R_a$ being as defined above;

(2) contacting the compound of formula (III) with a transition metal compound comprising Rh, Cu or Ru in presence of a hydroxy compound of formula ROH, R being as defined above, to obtain a compound of formula (IVa)

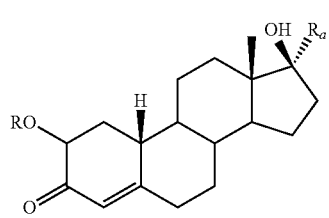

(IVa)

wherein R and $R_a$ being as defined above;

(3) contacting the compound of formula (IVa), wherein R and $R_a$ being as defined above, with an aromatization agent to obtain the compound of formula (I), wherein R being as defined above and X is the group

wherein $R_a$ is H, lower alkyl, alkenyl and alkynyl; and when $R_a$ is hydrogen, oxidizing the compound of formula (I) so obtained to yield the compound of formula (I) wherein X is O.

2. The method as set forth in claim 1 optionally comprising:

(i) oxidizing the compound (IVa), wherein $R_a$ is H, obtained in step (2) to obtain a compound of formula (IV)

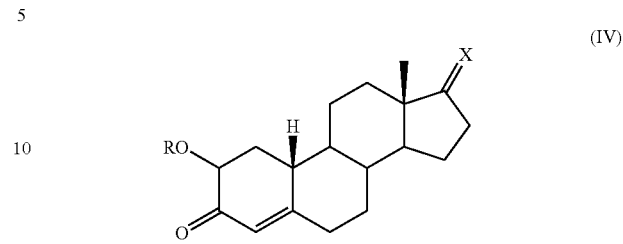

(IV)

wherein X is O and R being as defined above;

(ii) contacting the compound of formula (IV), wherein X is O and R being as defined above, with an aromatization agent to obtain the compound of formula (I), wherein X is O and R being as defined above; and reducing the compound of formula (I) so obtained, wherein X is O to yield the compound of formula (I) wherein R being as defined above and X is the group

wherein $R_a$ is H, lower alkyl, alkenyl or alkynyl.

3. The method as set forth in claim 1 wherein the sulfonyl azide derivative used to obtain the compounds of formula (III) is selected from the group consisting of benzenesulfonyl azide, methanesulfonyl azide, 4-toluenesulfonyl azide, 4-dodecylbenzenesulfonyl azide, 4-acetamidobenzenesulfonyl azide, 2,4,6-triisopropylbenzenesulfonyl azide, trifluoromethanesulfonyl azide, 4-carboxybenzenesulfonyl azide, 4-nitrobenzenesulfonyl azide, and imidazole-1-sulfonyl azide.

4. The method as set forth in claim 1 wherein the said transition metal used to obtain the compounds of formula (IVa) is selected from the group consisting of rhodium, ruthenium and copper.

5. The method as set forth in claim 1 wherein the aromatization agent used to obtain the compounds of formula (I) is a Pd—, Pt—, Rh—, Ru—, or Ni-based hydrogenation catalyst in the presence of a suitable hydrogen acceptor.

6. The method as set forth in claim 1 wherein the aromatization agent used to obtain the compounds of formula (I) is 2,3-dichloro-5,6-dicyanobenzoquinone (DDQ).

7. The method as set forth in claim 1 wherein the aromatization agent used to obtain the compounds of formula (I) is selenium dioxide ($SeO_2$).

8. The method as set forth in claim 1 wherein the aromatization agent used to obtain the compounds of formula (I) is the couple copper dibromide-lithium bromide ($CuBr_2$—LiBr).

9. The method as set forth in claim 1 wherein the aromatization agent used to obtain the compounds of formula (I) is a 1-dehydrogenating enzyme from a microorganism selected from the group consisting of *Bacterium* spp., *Corynebacterium* spp., *Cylindrocarpon* spp., *Mycobacterium* spp., *Nocardia* spp., *Pseudomonas* spp., and *Septomyxa* spp.

* * * * *